United States Patent [19]
Weinstein et al.

[11] Patent Number: 5,437,267
[45] Date of Patent: * Aug. 1, 1995

[54] DEVICE FOR DELIVERING AEROSOL TO THE NASAL MEMBRANES AND METHOD OF USE

[76] Inventors: Allan Weinstein, 9205 Pegasus Ct., Potomac, Md. 20854; Robert Weinstein, 62 Commonwealth Ave., Boston, Mass. 02116

[*] Notice: The portion of the term of this patent subsequent to Apr. 16, 2008 has been disclaimed.

[21] Appl. No.: 101,328

[22] Filed: Aug. 3, 1993

[51] Int. Cl.⁶ .................. A61M 11/00; A61M 15/08; A61M 16/10; A62B 7/00
[52] U.S. Cl. .................. 128/200.23; 128/203.12; 128/207.18
[58] Field of Search ............ 128/200.23, 200.24, 128/203.12, 203.13, 203.15, 203.14, 203.22, 203.23, 207.18; 604/94, 58

[56] References Cited

U.S. PATENT DOCUMENTS

| | | | |
|---|---|---|---|
| 3,367,330 | 2/1968 | Sierpiz | 128/200.23 |
| 4,969,578 | 11/1990 | Gander et al. | 128/200.23 |
| 5,002,048 | 3/1991 | Makiej, Jr. | 128/200.23 |
| 5,007,419 | 4/1991 | Weinstein et al. | 128/200.23 |

*Primary Examiner*—Kimberly L. Asher
*Attorney, Agent, or Firm*—Hopgood, Calimafde, Kalil & Judlowe

[57] ABSTRACT

A device for the intranasal delivery of a medicament regimen to the nasal membranes for the treatment of such conditions as rhinitis.

12 Claims, 3 Drawing Sheets

DEVICE FOR DELIVERING AEROSOL TO THE NASAL MEMBRANES AND METHOD OF USE

BACKGROUND OF THE INVENTION

1. The Field of the Invention

The present invention relates to a device for dispensing one or more medications to the nasal cavity.

2. The State of the Art

Respiratory ailments are frequently treated by topical medication which offers a rapid delivery of medication directly to the site of the problem. In contrast, oral or parental medication dosages require absorption and systemic distribution in order for a fraction of that medication to get to the desired site(s) and effect its therapeutic benefit. Because topical application is direct, smaller amounts of medication are generally required to achieve the same benefits as when the medication is given orally or parentally. Single canister inhalers, containing only one medication, are presently available for the treatment of obstructive lung disease. Multiple canister inhalers for the treatment of obstructive lung disorders are described, for example, in U.S. Pat. No. 5,007,419, the disclosure of which is incorporated herein by reference. Combined regimens of inhaled medication can be tailored to produce desired effects. It is often a desirable treatment regimen to combine one medication that provides immediate relief with a second dose of medication that produces long term (preventive) help.

Rhinitis is an inflammation of the nasal mucosal membrane. This inflammation is often accompanied by related symptoms, such as a runny, sore, or congested nose, and irritated eyes, depending upon the cause of the condition. Various types of therapies are available for applying a mist of medication through the nostrils to the nasal membranes. Typical therapeutic agents include adrenergically acting decongestants, anti-cholinergic agents, topical buffering compounds and lavaging solutions, "mast cell stabilizers," and corticosteroid anti-inflammatory agents.

There are some well-known drawbacks to the use of such medications when administered intranasally. For example, decongestant nasal sprays produce rebound nasal congestion and irritation. Patients desire immediate relief of their symptoms, whether caused by allergies or a "cold" (of viral and/or bacterial origin), and thus tend to favor the use of the most immediately and dramatically acting agent. However, in the search for immediate relief, overuse and failure to follow the prescribed or indicated pharmacological regime results in aggravation of the condition with rebound nasal congestion and irritation. Physicians are now tending to prescribe anti-inflammatory medications (e.g., corticosteroids) due to the recognition of the inflammatory nature of rhinitis and similar conditions. However, such medications are relatively much slower acting, and so patients tend to rely on immediately acting agents, a plethora of which are available in over-the-counter formulations. When patients fail to comply with the anti-inflammatory or prophylactic portion of their regime, they usually suffer the side effects of their improper use of these immediately acting agents.

Yet another problem with treating rhinitis and related or accompanying conditions is that patients are often required to have a multitude of inhalers and nasal applicators ready for use. Usually, each of these medications requires a different dosing regime. To compound problems, these differnt medications will often be provided in similar or identically appearing delivery devices; users often get confused as to which inhaler "is which." Such users also have to cope with a variety of mechanical configurations and operating techniques differing among the various devices, and thus are prone to errors in following their dosage regime. Therefore, users of multiple medications are faced, on the one hand, with a number of devices with similar or identical appearance but for different treatment purposes, or with a number of different types of devices having differing delivery techniques and again with different treatment purposes. Users of multiple individual delivery devices frequency make errors in the sequence in which these devices are used (i.e., in which the medicaments are taken); in some therapies, more than one medication is best administered in a particular sequence to provide the most benefit to the patient. In view of all of these difficulties, it is easy to see that patients often suffer needlessly merely due to the complexity of the organization and administration of their medication.

SUMMARY AND OBJECTS OF THE INVENTION

In view of the foregoing, it is an object of the present invention to provide a unitary device for the intranasal delivery of two or more different medications. Another object of the present invention is provide an intranasal delivery device in which two or more medications can be administered sequentially. The general object of this invention is to overcome the aforementioned problems and to improve patient compliance with a particular medication regime, thereby improving patient healing and comfort.

In brief, the intranasal delivery device of the present invention comprises a housing adapted to retain at least two canisters of different, atomizable medications. The housing can have a common outlet nozzle which is in fluid communication with the canisters or separate outlet nozzles for each canister. The common outlet nozzle and the individual outlet nozzles are adapted to be inserted into one or both nostrils for delivery of the medication housed in the canisters. The intranasal delivery device may also include a removable cap for covering the outlet nozzle. The device may also include a toggle lever which facilitates activation of the canisters in a prescribed sequence, and especially including indicia on the housing and/or the toggle to further aid in patient compliance. The device may be of a limited use, disposable type in which the canisters are not removable, or may be of an unlimited use type in which the canisters can be removed and replaced with the same or different medications.

DETAILED DESCRIPTION OF THE PREFERRED EMBODIMENTS

Broadly considered, the present invention provides an intranasal delivery device that contains a housing for two or more removable canisters of medication and at least one outlet nozzle adapted to be inserted into a nostril for dispensing the aerosol spray from each of the canisters.

The present nasal delivery device is different from bronchial inhaler devices in that the latter are intended to provide medication in a dispersed form for indirect administration to the trachea, bronchi, and/or lungs, rather than direct administration to the nasal cavity. That is, the medicament administered by bronchial delivery devices is not intended for delivery to the oral cavity into which it is released, but is intended to be inhaled to a deeper portion of the airway (i.e., the lungs and bronchi). In contrast, the present nasal delivery device is intended and designed to deliver a moist spray directly onto the nasal membrane.

The present device is particularly useful in the treatment of rhinitis, whether of allergic or non-allergic etiology, and other respiratory disorders which require the administration of a medicament to the nasal cavity. In oral and parenteral administration, the medicament is delivered to the blood stream, and so larger doses are required to deliver the proper dosage to the affected site. Direct delivery by intranasal administration allows for a comparatively smaller dosage to be used. Further, direct administration avoids or minimizes systemic side effects from the medication because absorption into the blood stream is only incidental.

Figure 1A:
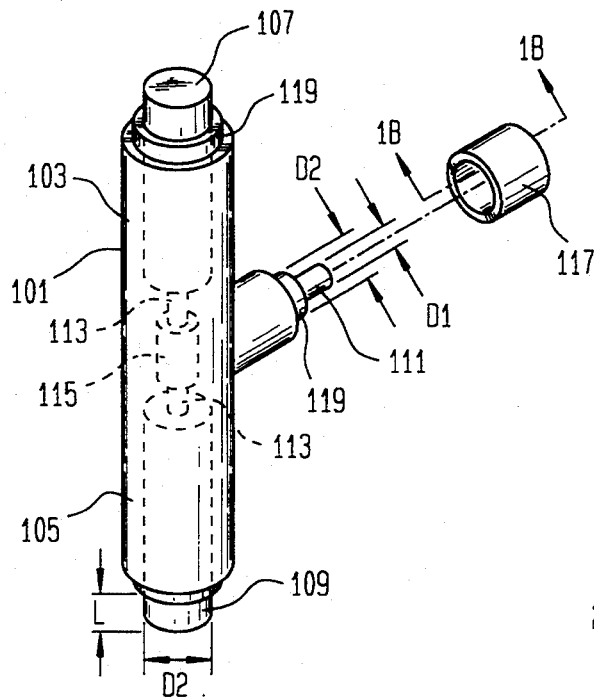
FIG. 1A depicts a perspective view of an intranasal delivery device and removable cap according to an embodiment of the present invention.

One embodiment of the present invention, as shown in FIG. 1A, generally comprises a housing 101 defining two chambers 103 and 105 adapted to receive and retain medicinal dispensing canisters 107 and 109 in the respective chambers. It is preferred to provide canisters which contain medication with a pressurized carrier (e.g., wherein releasing the pressure causes the carrier to exit the canister and carry the medication), although non-pressurized canisters or other types of containers suitable for dispensing the medication through the outlet nozzle can also be employed. Preferably, each of the canisters contains a different medication. The two medications can be administered simultaneously, sequentially, or at different times of the day. For example, one canister can include a decongestant, which is intended to be administered first to open the patient's nasal passages, after which a corticosteroid from the other canister can be administered (as an adjunct to a decongestant to prevent rebound nasal congestion). The housing has a common outlet nozzle 111 which is in fluid communication with the interior of the housing. Each of the canisters communicates through a conduit 113 with a common exit nozzle 115 which directs the medicament spray to the outlet nozzle. In use, the medication will flow from the canister through the conduit to the common exit nozzle, where it is redirected in as an atomized spray (aerosol) for delivery through the common outlet nozzle. The exit and outlet nozzles may, in some configurations, be incorporated into a unitary structure; conceptually, the exit nozzle provides the medicament in the desired form (e.g., an atomized spray) and the outlet nozzle directs or channels the exit nozzle effluent. The outlet nozzle is adapted to be of a size and geometry suitable for (at least partial) insertion into the nostril, and thus is of a size significantly smaller than the outlet adapted for administration through the oral cavity as required for bronchial inhaler devices.

Figure 1B:
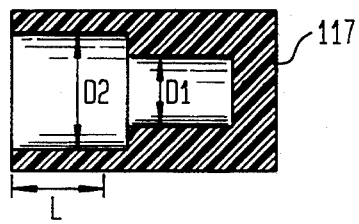
FIG. 1B depicts a cross-sectional view of a cap.

A cap 117 can be used to provide a sanitary closure means for the common outlet nozzle of the applicator. As shown in FIG. 1B, the cap can be designed to accommodate the common outlet nozzle or one of the canister ends protruding from the housing. A similar cap element and variations thereof is described in U.S. Pat. No. 5,007,419, the disclosure of which is incorporated herein by reference. In general, the cap is cylindrical with differing wall thicknesses. One diameter D1 corresponds to and can be placed over the outlet nozzle to provide sanitary protection. The cap also has another internal diameter D2, corresponding to the diameter of a canister, so that the cap can be placed on the housing over a particular canister to prevent its activation (i.e., release of medicament). When the cap is used to cover one of the canisters, the diameter D2 should be sized to provide a snug fit and abut the collar 119 at the opening of each of the chambers (103 and 105) and a similar collar 119 where the outlet nozzle 111 attaches to the housing. The cap has an interior portion of length L through diameter D2 adapted to accomodate the protruding portion of a canister, and has an interior length through both internal diameters D1 and D2 to accomodate the outlet nozzle. The medication is released from the canister by pushing the canister into the housing; in the preferred embodiment, in which the canisters are pressurized, pushing the canister towards the exit nozzle activates a valve in the canister (not shown) to release the pressurized contents. In such a configuration of the cap, when placed over the protruding end of the canister, pressing on the cap will not result in release of the contents of the capped canister. Accordingly, in the embodiment shown in FIG. 1A the user holds the device and squeezes the capped canister and the uncapped canister together; the uncapped canister is thus the one which is pushed into the housing to activate the release of medication.

The device can be fabricated for removable and/or replaceable canisters. Alternatively, the device can be fabricated as a disposable unit with non-removable canisters.

Figure 2:
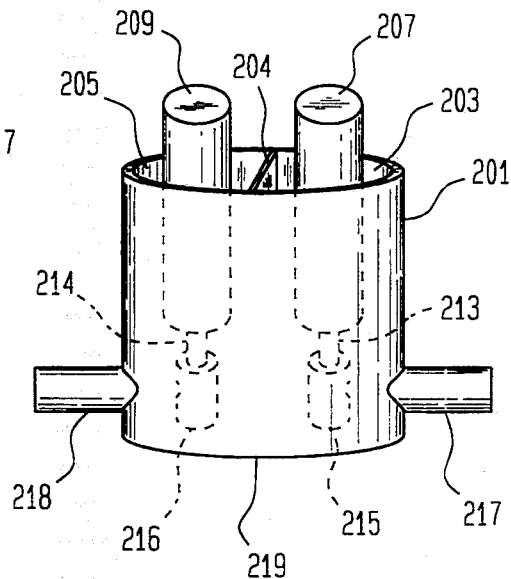
FIG. 2 depicts a perspective view of another embodiment of an intranasal delivery device of this invention.

Another embodiment of the nasal delivery device is shown in FIG. 2, in which a housing 201 having an essentially elliptical cross-section is provided with a chamber 203 adapted to receive pressurized medicament canisters; the chamber may optionally be divided by a partition 204 to provide a second chamber 205. The canisters 207 and 209 are provided in the chamber(s) in an orientation essentially parallel to each other and connected by conduits 213 and 214, respectively, to exit nozzles 215 and 216 which direct the spray to the outlet nozzles 217 and 218. In this configuration, the outlet nozzles are essentially on opposing sides of the device, which can facilitate administration of a different medication to each nostril (nasal passage). In operation, the user can activate the canister by squeezing together the protruding end of the canister and the bottom 219 of the device.

Figure 3A:
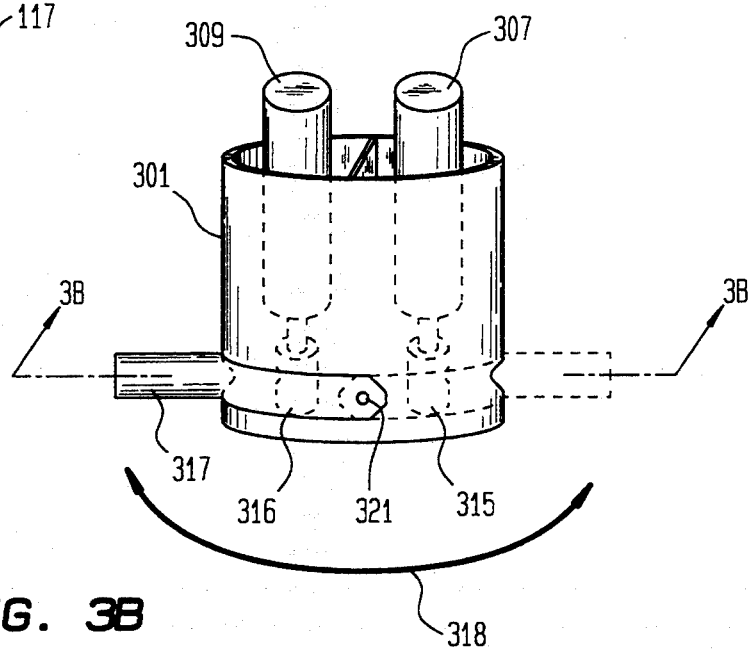
FIG. 3A depicts a perspective view of a modification of the embodiment depicted in FIG. 2 including a swivelable outlet nozzle.
Figure 3B:
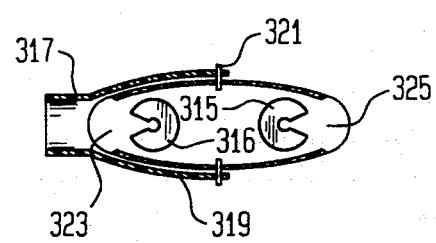
FIG. 3B is a cross-sectional view along line 3B—3B thereof.

An alternative to the embodiment shown in FIG. 2 is depicted in FIG. 3A, and generally includes a housing 301 in which are disposed two medicament canisters 307 and 309 in communication with their respective exit nozzles 355 and 316. A single outlet nozzle 317 which swivels as shown by the direction of arrow 318. The outlet nozzle is attached by arms 319 and pins 321 to the housing; other adjustable outlet nozzle configurations can also be used. In operation, the user can administer medication from canister 307 and then rotate or swivel the outlet nozzle to the position shown in order to administer medication from the other canister 309. The cross-sectional view shown in FIG. 3B, taken along line 3B—3B of FIG. 3A, depicts a swivelable outlet nozzle positioned in front of nozzle 316 and an associated port 323 through which the spray exits the housing; an opposing port 315 for the other canister remains uncovered.

Figure 4A:
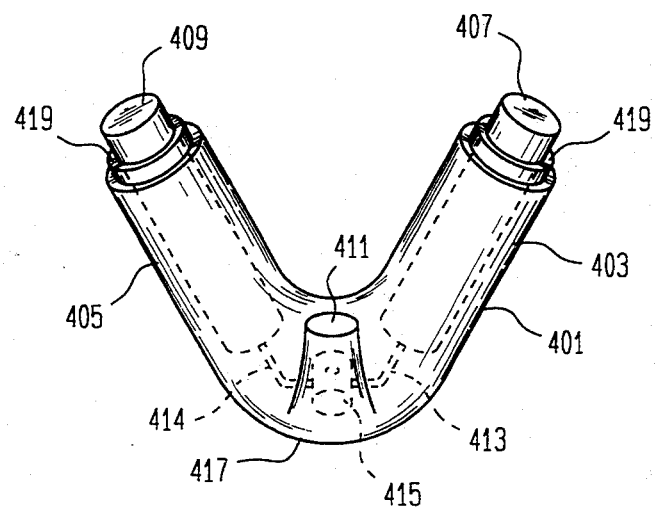
FIGS. 4A and 4B depict front and side views of yet another embodiment of an intranasal delivery device of this invention.
Figure 4B:
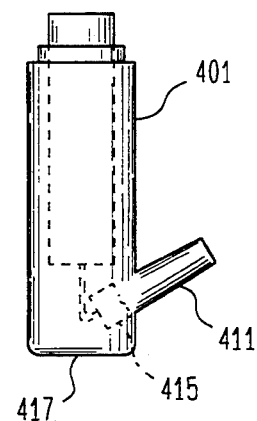

In yet another embodiment, the nasal applicator is provided with a V-shaped or wedge-like housing geometry 401 as shown in front view in FIG. 4A. The housing again provides chambers 403 and 405 in the legs of the "V" which are adapted to retain canisters 407 and 409 for delivery though the outlet nozzle 411. The canisters are connected with their respective conduits 413 and 414 to a common exit nozzle 415. In operation, when desiring to administer from canister 417, the user can squeeze together the protruding portion of that canister and the base or nadir of the "V" designated as 417. As seen more particularly in the side view depicted in FIG. 4B, the outlet nozzle 411 is preferably angled from the housing to facilitate application of the medication to the nasal membrane.

Figure 5A:
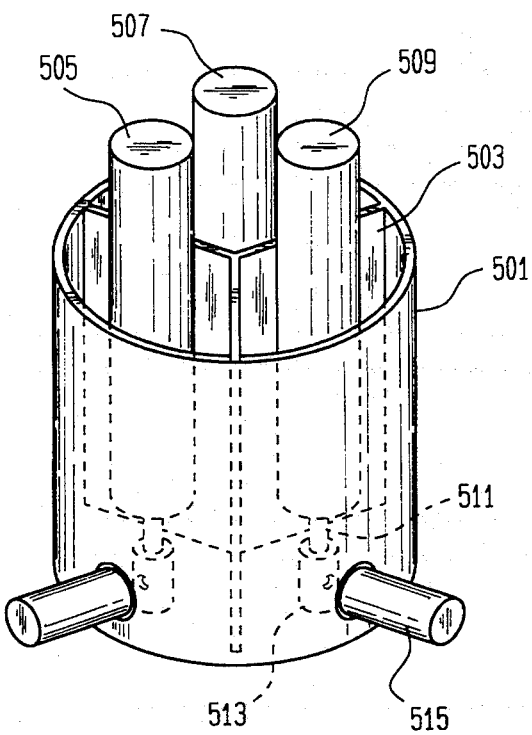
FIG. 5A depicts a perspective view of another embodiment of this invention including three medicament canisters.
Figure 5B:
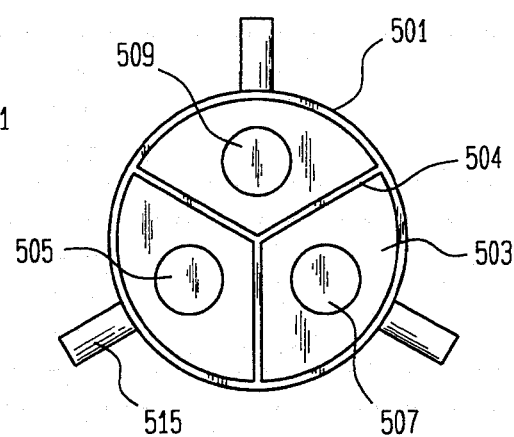
FIG. 5B depicts a top view thereof.

The present invention is also directed to nasal delivery devices having multiple medicament canisters, as shown in FIG. 5A. In this embodiment, the housing 501 is generally cylindrical and provides a chamber 503 in which are disposed three canisters 505, 507, and 509. Each of the canisters is shown with an associated conduit 511 and exit nozzle 513 for delivery through an associated outlet nozzle 515. FIG. 5B is a cross-sectional view through line 5B—5B in FIG. 5A, and additionally shows optional partitions 504 in the chamber to separate the canisters (analogous to that shown and described for the embodiment in FIG. 2).

Figure 6A:
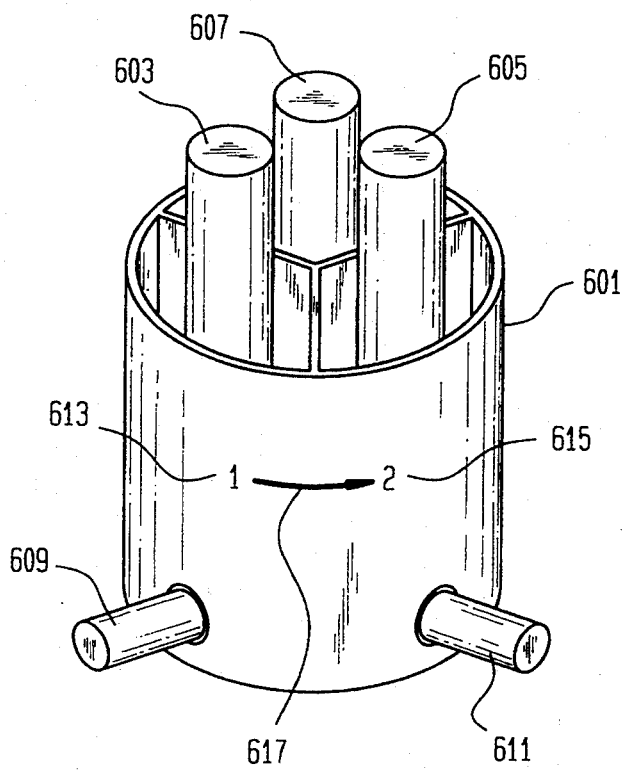
FIG. 6A depicts an embodiment similar to those shown in FIGS. 5A and 5B including prescriptive indicia on the housing.

FIG. 6A depicts a variation of the embodiment shown in FIGS. 5A and 5B. As shown, the device includes a housing 601 having a chamber in which are disposed three canisters 603, 605, and 607; outlet nozzle 609 is operably associated with canister 603, outlet nozzle 611 is operably associated with canister 605, and a third outlet nozzle (not shown) is operably associated with canister 607. On the outer wall of the housing are indicia 613 and 615 for directing the user (or care provider) in the prescribed sequential order of administration; an additional indicium arrow 617 (or other symbol) can be used instead of or in addition to the other indicia to facilitate using the device. Alternatively, the canisters can be color-coded and the indicia correspondingly color-coded to indicate the sequence of administration; the outlet nozzles can likewise be color-coded and/or include indicia thereon indicating the sequence of administration. The indicia, instead of prescribing the sequential order of administration, can include other or additional information, such as the contents of the various canisters or the symptoms to be treated with each canister.

Figure 6B:
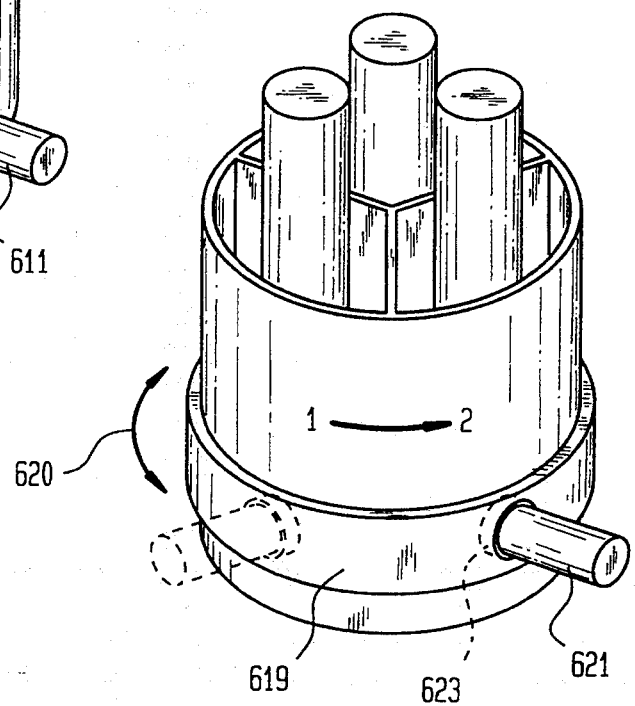
FIG. 6B depicts such an embodiment including a swivelable (rotatable) outlet nozzle.

Shown in FIG. 6B is a variation of a positionally adjustable outlet nozzle analogous to that shown in FIG. 3. With the circular housing shown in any of the embodiments depicted in FIGS. 5A, 5B, or 6A, the positionally adjustable outlet nozzle generally comprises a ring 619 disposed about and rotatable about the circumference of the housing. The user rotates the ring along the direction of arrow 620 to align the outlet nozzle 621 with an exit port 623 in the housing through which the exit nozzle associated with a particular canister sprays the medicament. When combined with the indicia shown in FIG. 6A, the user merely needs to rotate the outlet nozzle on the ring to the appropriately indicated port to dispense the medicament in the prescribed sequence.

Figure 7:
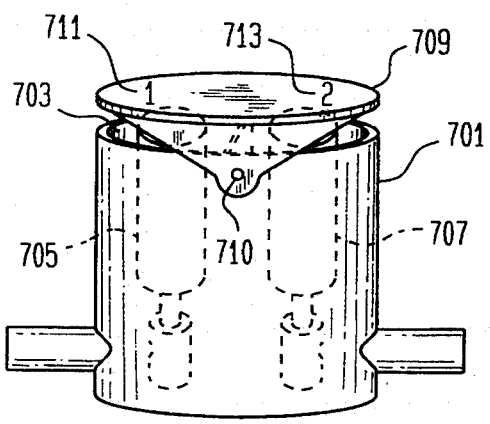
FIG. 7 depicts a modification of the embodiment depicted in FIG. 2 including a toggle.

Yet another embodiment is shown in FIG. 7, a device having the same general structure of the embodiment shown in FIGS. 2 or 3; namely, a housing 701 open at the top and defining a chamber 703 in which are disposed canisters 705 and 707. Attached near the opening of the chamber is a toggle 709, a lever rotatably attached to the housing by pins 710. The top surface of the toggle preferably includes indicia 7111 and 713 associated with each canister in the device to facilitate the prescribed sequential administration of medicament. The user merely presses down on the end of the toggle (i.e., approximately where the indicia are shown in the figure) to activate release of the medicament and is directed in the order of administration by the indicia thereon. The placement and design of the toggle should be such that one of the ends of the toggle must be pushed down to administer the medicament.

The present invention thus provides a nasal delivery device in which the canisters can be disposed or arranged with respect to each other in a linear, parallel, angular, or circular relationship.

While the foregoing embodiments have been described to illustrate and exemplify the present invention, various modifications may be made by the artisan upon a perusal of this specification, and such changes are intended to be within the scope and spirit of the invention as defined by the claims.

What is claimed is:

1. A device for delivering medication to a patients' nasal membranes and minimizing systemic side effects from administering the same, comprising:

a housing having first and second chambers;

said first chamber having a first internal compartment and a first removable canister of a first medication housed in said first compartment;

said second chamber having a second internal compartment and a second removable canister of a second medication housed in said second compartment;

said housing further having at least one outlet nozzle selected from (a) at least one common outlet nozzle in fluid communication with said canisters of medication and means for independently allowing aerosol spray from either of said first or second canisters to be discretely released through an exit nozzle to said common outlet nozzle and (b) a separate outlet nozzle in fluid communication with each of said first and second canisters of medication and means for independently allowing aerosol spray from one of said canisters to be discretely released through an exit nozzle to said separate outlet nozzle associated therewith;

means for delivering aerosol directly onto a patient's nasal membranes and minimizing systemic side effects from said administration; and means for indicating at least one of (a) a prescribed dispensing sequence of medicament from said aerosol canisters received in said chambers, (b) the medicament contained in each of said canisters, and (c) patient symptoms to be treated by each of the medicaments released as aerosols from said canister.

2. The device as defined by claim 1, wherein said common outlet nozzle is positionally adjustable between each of said exit nozzles.

3. The device as defined by claim 1, wherein the canisters are oriented essentially parallel to each other, and further comprising toggle means rotatably mounted on said housing for selectively activating the dispensing of medicament from a particular canister.

4. The device as defined by claim 3, comprising indicia on said toggle of the prescribed dispensing sequence.

5. The device as defined by claim 1, wherein the canisters are disposed in a linear, parallel, angular, or circular relationship with respect to each other.

6. The device as defined by claim 1, further comprising a cap adapted to fit over and operably cover at least one of said outlet nozzles.

7. The device as defined by claim 1, comprising at least said indicia on the housing of the prescribed dispensing sequence.

8. The device as defined by claim 1, wherein the medicaments are selected from the group consisting of adrenergically acting decongestants, anti-cholinergic agents, topical buffering compounds and lavaging solutions, mast cell stabilizers, corticosteroid anti-inflammatory agents, and mixtures thereof.

9. The device as defined by claim 1, wherein the medicaments comprise a decongestant and an anti-inflammatory agent.

10. A method for facilitating patient compliance in the equential intranasal administration of at least two medicaments to a patient in need thereof, which method comprises:

providing a housing having first and second chambers;

providing in said first chamber a first internal compartment and a first removable canister of a first medication housed in said first compartment;

providing in said second chamber a second internal compartment and a second removable canister of a second medication housed in said second compartment;

providing on said housing at least one outlet nozzle selected from (a) at least one common outlet nozzle in fluid communication with said canisters of medication and providing means for independently allowing aerosol spray from either of said first or second canisters to be discretely released through an exit nozzle to said common outlet nozzle and (b) a separate outlet nozzle in fluid communication with each of said canisters of medication and providing means for independently allowing aerosol spray from each of said first and second canisters to be discretely released through an exit nozzle to said separate outlet nozzle associated therewith;

providing means for delivering aerosol directly onto a patient's nasal membranes and minimizing systemic side effects of said administration; and providing means for indicating at least one of (a) a prescribed dispensing sequence of medicament from said aerosol canisters received in said chambers, (b) the medicament contained in each of said canisters, and (c) patient symptoms to be treated by each of the medicaments released as aerosols from said canister.

11. The device as defined by claim 9, wherein the medicaments are selected from the group consisting of adrenergically acting decongestants, anti-cholinergic agents, topical buffering compounds and lavaging solutions, mast cell stabilizers, corticosteroid anti-inflammatory agents, and mixtures thereof.

12. The device as defined by claim 9, wherein the medicaments comprise a decongestant and an anti-inflammatory agent.

* * * * *